(12) United States Patent
Chandrasekaran et al.

(10) Patent No.: US 6,554,827 B2
(45) Date of Patent: Apr. 29, 2003

(54) RADIO FREQUENCY ABLATION SYSTEM

(75) Inventors: Verivada Chandru Chandrasekaran, Mercer Island, WA (US); Zihong Guo, Bellevue, WA (US); Brandon Shuman, Kirkland, WA (US); Robert L. Barry, Kirkland, WA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/735,077

(22) Filed: Dec. 11, 2000

(65) Prior Publication Data

US 2002/0072740 A1 Jun. 13, 2002

(51) Int. Cl.[7] .............................................. A61B 18/18
(52) U.S. Cl. ........................................... 606/41; 607/99
(58) Field of Search ................................ 606/41, 32–34; 607/96, 100–101, 99

(56) References Cited

U.S. PATENT DOCUMENTS

| | | | | |
|---|---|---|---|---|
| 4,643,186 A | * | 2/1987 | Rosen et al. ................. | 606/159 |
| 5,125,928 A | * | 6/1992 | Parins et al. ................. | 606/48 |
| 5,178,618 A | * | 1/1993 | Kandarpa ................... | 606/195 |
| 5,366,443 A | * | 11/1994 | Eggers et al. ................ | 606/31 |
| 5,846,239 A | * | 12/1998 | Swanson et al. ............. | 606/41 |
| 6,120,499 A | * | 9/2000 | Dickens et al. .............. | 600/374 |
| 6,228,109 B1 | * | 5/2001 | Tu et al. ..................... | 606/41 |
| 6,325,797 B1 | * | 12/2001 | Stewart et al. .............. | 606/41 |

* cited by examiner

Primary Examiner—Lee Cohen
Assistant Examiner—Henry M. Johnson
(74) Attorney, Agent, or Firm—Christensen O'Connor Johnson Kindness PLLC

(57) ABSTRACT

An RF ablation system includes a catheter and an RF electrode that delivers RF electrical energy to the site of an occlusion. The system includes a mechanism for minimizing the likelihood that RF electrical energy will be applied directly to the vessel wall. In one embodiment of the invention, the catheter includes a number of tissue expanding jaws to engage a vessel wall and push the vessel wall away from the electrode to shield vessel walls from the electrode. In yet another embodiment of the invention, the electrode has a spiraled distal end with a radius that is larger than the radius of the catheter, such that the electrode engages the vessel wall and pushes the wall away from a conducting portion of the electrode. The portion of the electrode that engages the vessel wall is preferably coated with an insulating material to prevent delivery of RF electrical energy directly to the vessel wall.

4 Claims, 3 Drawing Sheets

RADIO FREQUENCY ABLATION SYSTEM

FIELD OF THE INVENTION

The present invention relates to medical devices in general, and in particular to radio frequency atherectomy devices for removing intravascular occlusions.

BACKGROUND OF THE INVENTION

One of the most common types of vascular disease is characterized by reduced blood flow due to the presence of partial or total occlusions in a vessel. Such occlusions can contribute to the incidence of hypertension, cardiac arrest or stroke. To restore blood flow in an occluded vessel, it has become a routine procedure to bypass the occlusion with a healthy vessel obtained from elsewhere in the body. While bypass techniques are often successful, the procedure is fairly traumatic because the surgeon must access the blocked vessel externally in order to install the bypass.

One example of a less invasive technique used to restore blood flow requires the advancement of an atherectomy device including a cutting or grinding mechanism through the patient's vasculature to the point of the occlusion. The cutting or grinding mechanism is then rotated at high speed to remove the occlusion from inside the vessel. While less traumatic than bypass surgery, the technique can be limited to the treatment of vessels through which the physician can route the atherectomy device. In addition, the cutting mechanisms are typically not very aggressive, thereby increasing the amount of time required to perform the procedure.

One technique that may offer some advantages over traditional mechanical atherectomy devices is to use RF electrical energy to remove an occlusion. The advantage of using RF electrical ablation energy is that the electrode can be made sufficiently flexible such that it can be routed through virtually any vessel. In addition, each RF pulse removes a greater amount of occluding material, thereby reducing the time required to complete the procedure.

As with any intravascular procedure, precautions must be taken to minimize the likelihood that RF electrical energy will perforate a vessel wall. Therefore, there is a need for an RF ablation system that minimizes the likelihood of vessel perforation while maintaining the advantages of RF ablation.

SUMMARY OF THE INVENTION

A radio frequency (RF) ablation system includes a catheter through which an RF electrode is routed to the point of a vascular deposit or occlusion. The system has a mechanism for pushing a vessel wall away from an area near the RF electrode that delivers an RF pulse.

In one embodiment of the invention, the catheter includes a number of tissue expanding jaws that can be engaged with the vessel wall and biased radially outward in order to move a vessel wall away from the RF electrode.

In another embodiment of the invention, the RF electrode includes a coiled portion at its distal end. The coiled portion has a radius that is larger than a radius of the catheter that delivers the electrode. The coiled portion of the electrode engages the vessel wall and moves it away from the area of the electrode that delivers an RF pulse.

In yet another embodiment of the invention, the RF electrode has a ring that surrounds a center portion of the electrode. The ring has a radius that is larger than the radius of the catheter through which the RF electrode is routed. The ring engages the vessel wall and moves it away from an area of the center portion of the electrode that delivers an RF pulse.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENTS

As indicated above, the present invention is an RF ablation system that reduces the likelihood that RF electrical energy will be applied to a vessel wall.

Figure 1A:
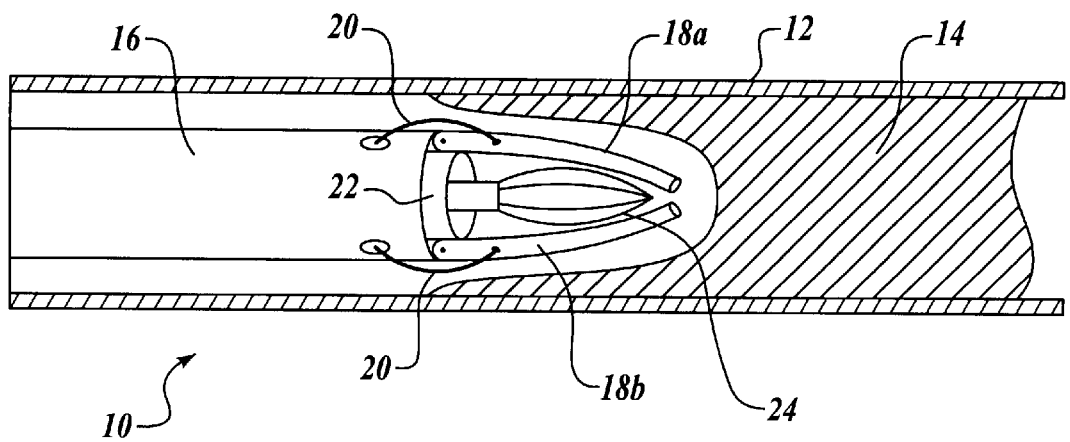
FIG. 1A illustrates an RF ablation system including a pair of tissue expanding jaws shown in a closed position.

FIG. 1A illustrates a first embodiment of an RF ablation system according to the present invention. An RF ablation system 10 is routed within a vessel 12 that is partially or totally blocked by deposits or an occlusion 14. The ablation system 10 includes an outer catheter 16 with a tissue expander comprising a pair of tissue expanding jaws 18a, 18b at its distal end. The jaws 18a and 18b are hinged to a ring 22 disposed at the distal end of the catheter 16. Each of the jaws 18a, 18b may be opened using a pull wire 20 or like mechanism that allows the jaws to selectively biased outward.

Routed through the catheter 16 is an RF ablation electrode 24 that is coupled at its proximal end to a source of RF electrical energy (not shown). The RF electrode 24 may include one or more conducting wires that expand radially outward at their distal end to create a number of contact points at which RF electrical energy is delivered to the deposits or occlusion.

Figure 1B:
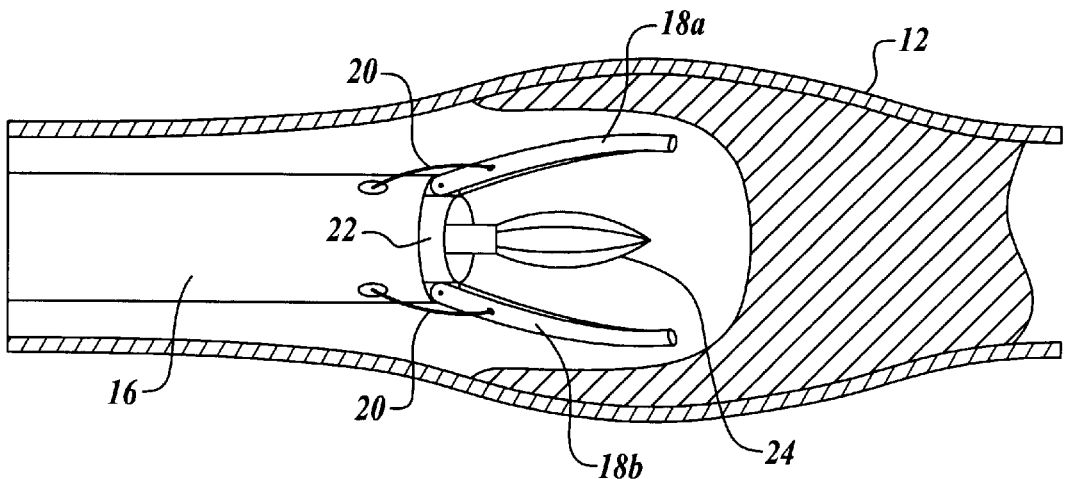
FIG. 1B illustrates an RF ablation system as shown in FIG. 1A with the tissue expanding jaws shown in an open position.

FIG. 1B illustrates the atherectomy device 10 with the tissue expanding jaws 18a and 18b shown in an outwardly biased condition. By pulling proximally on the pull wires 20, the tissue expanding jaws 18a, 18b are biased radially outward in the vessel 12, thereby contacting and moving the vessel wall away from the RF ablation electrode 24. The RF ablation electrode 24 preferably remains within the area contained within the expanded jaws 18a and 18b in order to limit the likelihood that the electrode 24 will contact a vessel wall. With the jaws expanded, the RF ablation electrode 24 delivers a pulse of RF electrical energy to ablate an area of the occlusion 14. If desired, aspiration can be applied to the catheter 16 in order to remove ablated deposits from the vessel.

Although the presently preferred embodiment of the invention utilizes pull wires 20 in order to open the jaws 18a and 18b, it will be appreciated that other mechanisms such as springs, or the use of metals having shape memory could be used to bias the jaws radially outward. Furthermore, the present invention is not limited to the use of two jaws. For example, three or more jaws could also be used at the distal end of the catheter 16 in order to bias the vessel wall radially outward and away from the RF ablation electrode.

FIGS. 2–5 illustrate a number of alternative embodiments of RF ablation electrodes according to the present invention. In each of these embodiments, the diameter of the electrode at its distal end is larger than the diameter of the catheter used to deliver the RF ablation electrode to the occlusion site to form a tissue expander.

Figure 2:
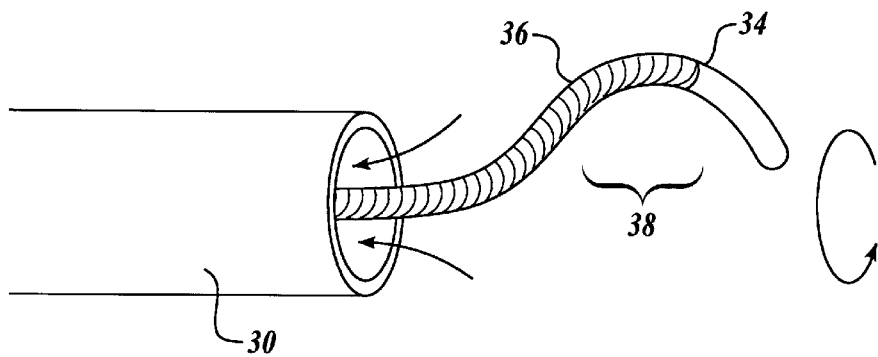
FIG. 2 illustrates an RF ablation electrode according to another embodiment of the present invention.

In FIG. 2, a catheter 30 delivers an RF ablation electrode 34 to the site of an occlusion in a vessel. The electrode 34 has a "hook-like" or partial corkscrew shape at its distal end such that the electrode 34 bends radially outward at a point proximal to the distal tip before curving radially inward at its distal tip. In some instances, the RF ablation electrode 34 may be partially covered with an insulating material 36 such that only the distal tip of the electrode delivers RF energy to the occlusion. A radially extended portion 38 of the electrode contacts a vessel wall and displaces it away from the distal tip of the electrode such that it is less likely that the distal tip of the electrode will contact the vessel wall during the ablation procedure. In operation, a physician rotates the distal end of the RF ablation electrode 34 around its longitudinal axis in order to ensure the uniform delivery of RF electrical energy to the site of the occlusion.

Figure 3:
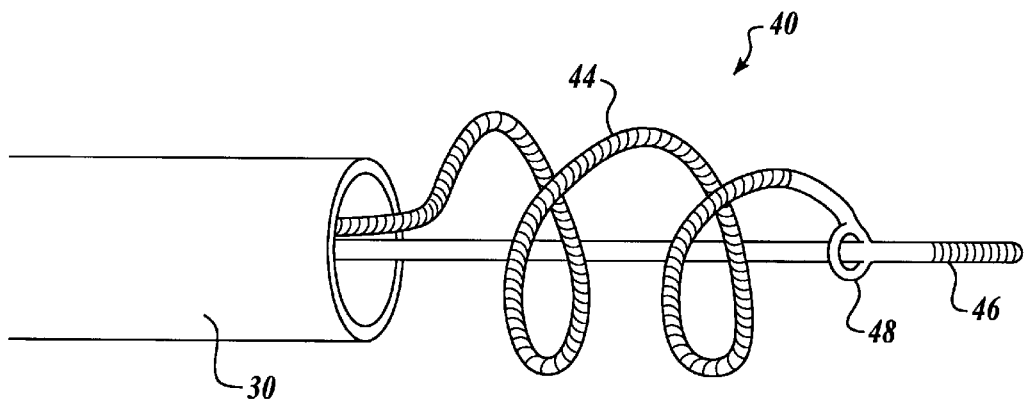
FIG. 3 illustrates an RF ablation electrode according to yet another embodiment of the present invention.

FIG. 3 illustrates another alternative embodiment of an RF ablation electrode 40 according to the present invention. A catheter 30 delivers the RF ablation electrode 40 to a site of an occlusion. The RF ablation electrode 40 has a distal end that spirals in a corkscrew-like fashion. The electrode 40 has a radius that extends outward to a maximum diameter at a point proximal to the distal end and spirals radially inward to a minimum diameter at the distal tip of the electrode. The electrode may be covered with an insulating material 44 over its length, with the exception of an area at the distal tip to ensure that RF ablation energy is delivered primarily to the occlusion at the distal tip of the electrode.

In some instances, it is desirable that the RE ablation electrode 40 be delivered over a guide wire 46. Therefore, the distal tip of the electrode may include a ring 48 or other guidewire routing device through which the guide wire 46 is threaded. The guide wire 46 is also preferably coated with a nonconducting material such that it does not conduct RF electrical energy when the energy is delivered to the RF electrode 40.

The spiral shape of the electrode 40 near its distal end serves to push the vessel walls radially outward in order to minimize the likelihood that RF ablation energy delivered from the distal tip of the electrode will contact the vessel wall. The electrode 40 is preferably made from a relatively flexible metal such as Nitenol™, so that it can be withdrawn into the catheter 30 in order to compress the spirals at the distal end. However, when the electrode 40 is pushed out of the distal end of the catheter 30, the electrode assumes its spiral shape. If the metal that comprises the RF electrode is not sufficiently conductive, it is possible to secure a more conductive wire to it in order to deliver the RF electrical energy to the site of the occlusion.

Figure 4:
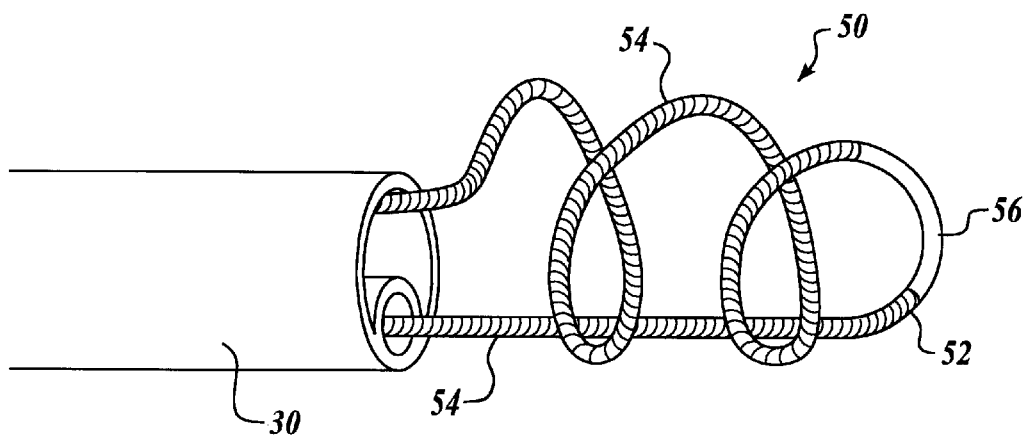
FIG. 4 illustrates an RF ablation electrode according to yet another embodiment of the present invention.

FIG. 4 shows another alternative embodiment of an RF ablation electrode 50 according to the present invention. A catheter 30 delivers the RF ablation electrode 50 to a site of an occlusion. The distal end of the RF ablation electrode 50 has a spiral corkscrew shape, similar to the embodiment shown in FIG. 3. However, at the distal end of the electrode where the spiraled portion has a minimum radius, the electrode returns as a straight wire to the proximal end of the catheter 30. This portion of the electrode forms a pull wire 52 that can be used to steer the electrode within the vessel. Preferably, this RF ablation electrode 50 is covered with an insulating material 54 over its entire length, with the exception of an area 56 at or near its distal tip, in order to prevent the delivery of RF ablation energy in undesired locations within the vessel.

Figure 5:
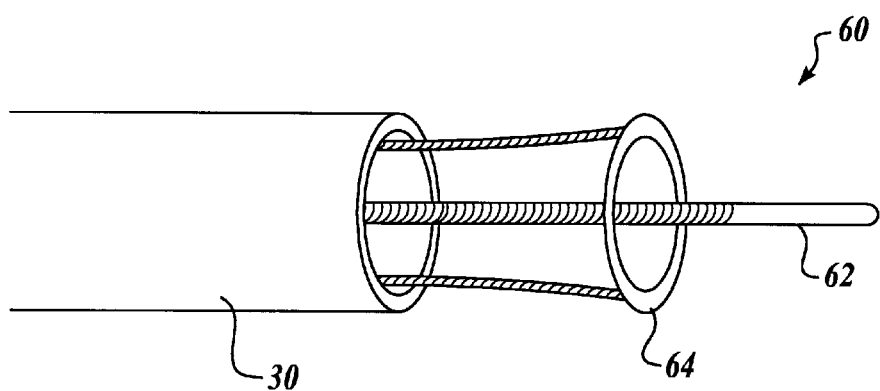
FIG. 5 illustrates a bipolar RF electrode in accordance with yet another embodiment of the present invention.

FIG. 5 illustrates yet another embodiment of the present invention. In this embodiment, a catheter 30 delivers a bipolar electrode 60 having a center conducting electrode 62 and a proximal ring electrode 64 that surrounds the center conducting electrode 62. Each of the electrodes 62 and 64 are coupled to the source of RF electrical energy such that an RF pulse travels between them and an external patient pad is not required to complete the RF electrical circuit. The proximal ring electrode 64 that surrounds the center conducting electrode 62 is preferably made of a flexible metal such that it can be routed within the catheter and will pop open to its desired shape once it is pushed out the distal end of the catheter 30. The proximal ring electrode 64 may simply surround the center conducting electrode 62, or may contain a support through which the center conducting electrode is routed in order to maintain the spacing of the center electrode with respect to the proximal ring electrode 64. Preferably, both the center electrode 62 and the proximal ring electrode 64 are covered with an insulating material, except for specific regions where it is desired that the electrodes conduct the RF ablation energy. In operation, the proximal ring electrode 64 engages the vessel wall and pushes it away from the center conducting electrode 62 such that the chance that the center conducting electrode will engage the vessel wall is reduced.

As can be seen from the above, the present invention provides a simple mechanism for delivering RF ablation energy to an occlusion site in the vessel while minimizing the chance that RF ablation energy will be delivered directly to the vessel wall.

While the preferred embodiment of the invention has been illustrated and described, it will be appreciated that various changes can be made therein without departing from scope of the invention. It is therefore intended that the scope of the invention be determined from the following claims and equivalents thereto.

The embodiments of the invention in which an exclusive property or privilege is claimed are defined as follows:

1. A system for removing deposits from a vessel, comprising:

a catheter;

an electrode routed within the catheter that delivers RF ablation energy to remove deposits within the vessel; and a tissue expander positioned adjacent the electrode that engages a portion of a vessel wall and moves it radially away from an area of the electrode when the electrode delivers the RF ablation energy to the deposits.

2. A system for removing deposits from a vessel, comprising:

a catheter;

an electrode routed within the catheter that delivers RF ablation energy to remove deposits within the vessel; and a tissue expander that engages a portion of a vessel wall and moves it away from an area of the electrode that delivers the RF ablation energy to the deposits, wherein the tissue expander includes a number of tissue expanding jaws that can be radially expanded.

3. The system of claim 2, wherein the tissue expanding jaws are made of a spring material that is biased radially outward.

4. A system for removing deposits from a vessel, comprising:

a catheter;

an electrode routed within the catheter that delivers RF ablation energy to remove deposits within the vessel; and a tissue expander including a number of jaws that are moved radially outward by pull wires to engage a portion of a vessel wall and move it away from an area of the electrode that delivers the RF ablation energy to the deposits.

* * * * *

UNITED STATES PATENT AND TRADEMARK OFFICE
CERTIFICATE OF CORRECTION

PATENT NO. : 6,554,827 B2
DATED : April 29, 2003
INVENTOR(S) : V.C. Chandrasekaran et al.

It is certified that error appears in the above-identified patent and that said Letters Patent is hereby corrected as shown below:

<u>Title page,</u>
Item [56], References Cited, insert
-- 5,320,627    7/1994     Sorensen et al.
   5,542,928    8/1996     Evans et al.
   5,743,900    4/1998     Hara
   RE35,787     5/1998     Nash et al.
   5,820,629    10/1998    Cox
   6,036,689    12/11/00   Tu et al. --

Signed and Sealed this

Third Day of August, 2004

JON W. DUDAS
*Acting Director of the United States Patent and Trademark Office*